United States Patent [19]

Ono

[11] 4,198,565
[45] Apr. 15, 1980

[54] CHARGED PARTICLE BEAM SCANNING APPARATUS

[75] Inventor: Katsuhiro Ono, Kawasaki, Japan

[73] Assignee: Tokyo Shibaura Electric Co., Ltd., Kawasaki, Japan

[21] Appl. No.: 853,832

[22] Filed: Nov. 21, 1977

[30] Foreign Application Priority Data

Nov. 26, 1976 [JP] Japan .................... 51-141831

[51] Int. Cl.² ........................................... H01J 37/00
[52] U.S. Cl. ............................... 250/399; 250/398; 250/396 ML
[58] Field of Search .......... 250/396 R, 396 ML, 398, 250/490, 492 R, 298, 399; 313/361, 421, 442; 335/210, 213

[56] References Cited

U.S. PATENT DOCUMENTS

| 3,287,558 | 11/1966 | Bly et al. ................ 250/396 |
| 3,516,037 | 6/1970 | Enge .................... 250/398 |
| 3,629,578 | 12/1971 | LePoole .................. 250/398 |
| 3,867,635 | 2/1975 | Brown et al. ............. 250/396 |

FOREIGN PATENT DOCUMENTS 1269017 3/1972 United Kingdom.

OTHER PUBLICATIONS

Holiday et al. "Physics" John Wiley & Sons Inc., 1966 pp. 816–817.

Primary Examiner—Bruce C. Anderson
Attorney, Agent, or Firm—Cushman, Darby & Cushman

[57] ABSTRACT

A charged particle beam scanning apparatus includes a deflector for a beam of charged particles which includes a magnetic field generator to supply an incoming electron beam with a magnetic field whose intensity grows higher in the opposite direction to that in which the beam is deflected.

10 Claims, 15 Drawing Figures

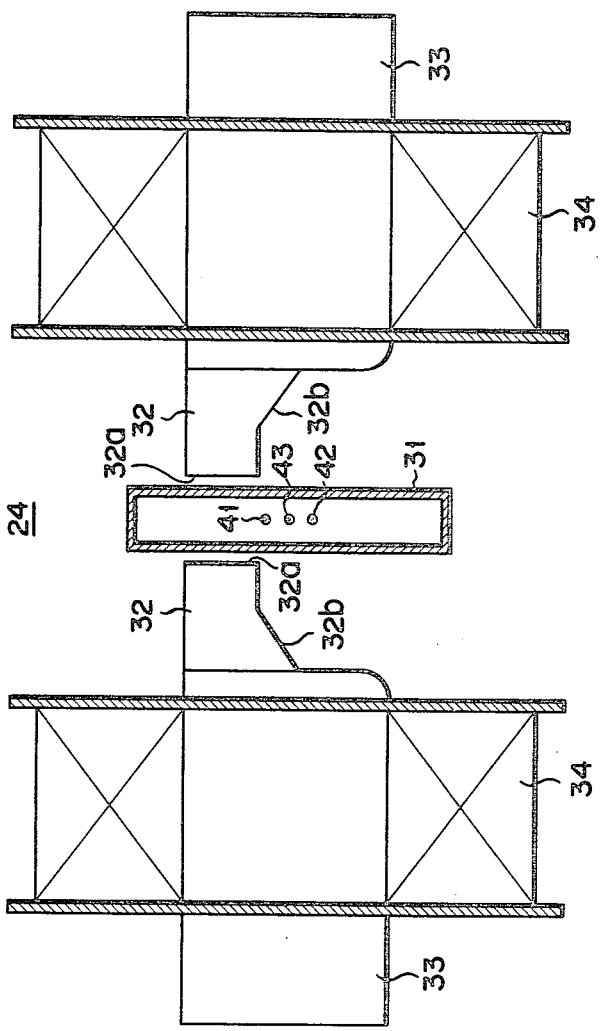

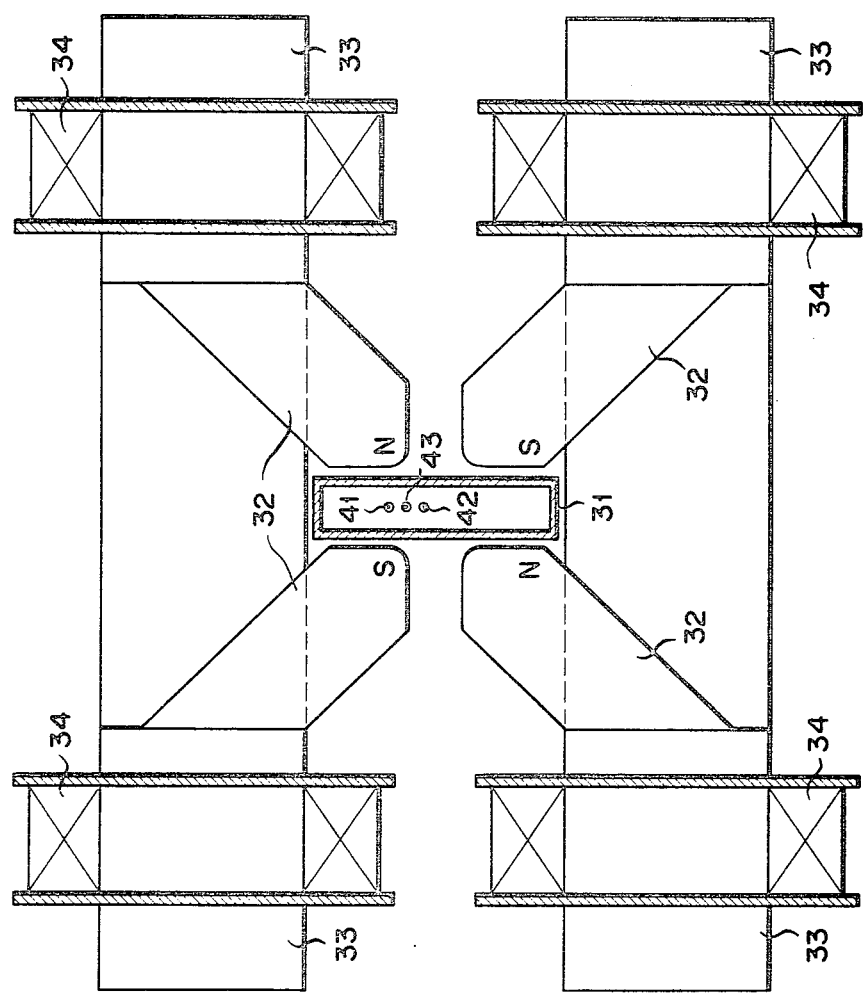
F I G. 12

CHARGED PARTICLE BEAM SCANNING APPARATUS

This invention relates to a charged particle beam scanning apparatus designed to deflect a beam of charged particles, for example, electron beams accelerated by a linear accelerator to the prescribed position.

Various fields of science and industry utilize a charged particle beam scanning apparatus designed to deflect a beam of charged particles accelerated by a linear accelerator using a microwave tube to the prescribed position. In the field of medical treatment implements, charged particles are directly irradiated on a patient, or an X-ray target to generate X-rays.

An attempt has hitherto been made to render the abovementioned charged particle beam scanning apparatus as compact as possible by deflecting a beam of charged particles accelerated by an accelerator at the prescribed angle toward a foreground subject. A deflector designed to deflect an electron beam at an angle of substantially 90° is more widely accepted particularly in the field of medical treatment implements than the type which deflects an electron beam at an angle of substantially 270°, because the former type admits to miniaturization.

As proposed to date, said former type of charged particle scanning apparatus comprises, as shown in FIG. 1, a pair of magnetic poles 2 and a pair of coils 3 positioned on both sides of a vacuum deflector 1 and deflects an electron beam by a magnetic field generated across both magnetic poles 2. Where, in this case, accelerated by a linear accelerator, an electron beam changes in energy and broadens, and presents deflections corresponding to said change and broadening. Namely, as seen from FIG. 2, an electron beam 4 deflected in a deflector 1 have a wide distribution defined on one side by higher energy electrons running along an orbit 5 and on the other by lower energy electrons conducted along an orbit 6. Referential numeral 7 denotes the deflection of orbit of that portion of an electron beam which has the most probable energy $E_0$ constituted by the largest number of electrons. As apparent from FIG. 3, the intensities of the beams being deflected are generally so distributed as to have an extension of about ±5% from the most probable energy $E_0$. The prior art beam of having the above-mentioned intensity distribution presents difficulties in being irradiated on a foreground subject efficiently at high precision. Where such an electron beam was made to impinge on an X-ray target, then X-rays even conducted through, for example, a flattening filter undesirably indicated an irregular distribution of beam when applied to a foreground subject. As seen from FIG. 4, X-rays which were so adjusted as to indicate a uniform intensity as shown by a solid line were easy to present an irregular intensity as seen from the broken line of FIG. 4 when energy spectrum shown in FIG. 3 was slightly fractuated. A dose rate of X-rays penetrating a human body used as a foreground subject should always be fixed when applied under the same condition in order to minimize the destruction of the normal tissue thereof. However, the prior art charged particle scanning apparatus did not meet this requirement.

In an aspect of the present invention there is provided a charged particle beam scanning apparatus comprising a charged particle source for emitting a beam of charged particles; a linear accelerator for accelerating a beam of charged particles issued from said charged particle source; and a deflection device for deflecting a beam of accelerated charged particles at the prescribed angle around a reference axis, said deflection device including a magnet field generator to supply an incoming beam of charged particles with a magnetic field whose intensity grows higher in the opposite direction to that in which the beam of charged particles is deflected.

It is accordingly the object of this invention to provide a charged particle beam scanning apparatus which prevents a beam of charged particles accelerated by an accelerator from being widely deflected in spite of application of a small deflector, and concentratedly deflects said beam at the prescribed angles about a reference axis toward a foreground subject.

This invention can be more fully understood from the following detailed description when taken in conjunction with the accompanying drawings, in which.

Figure 2:
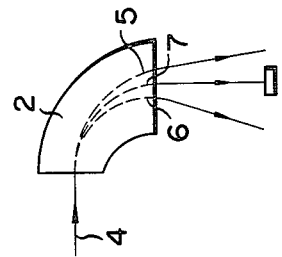
FIG. 2 is a schematic side view of the deflector of FIG. 1, showing its operation.
Figure 1:
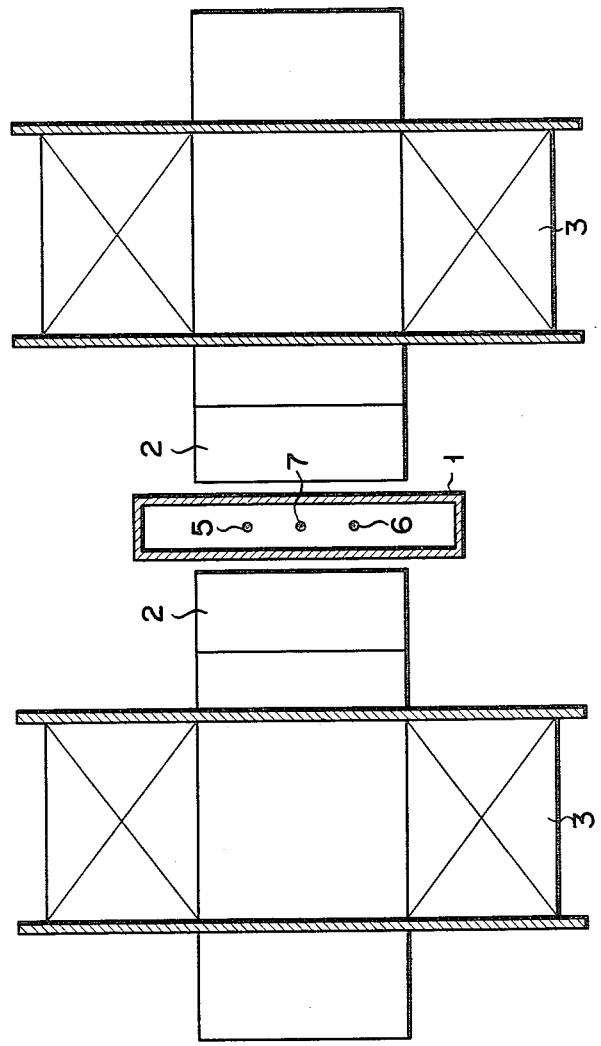
FIG. 1 is a schematical cross sectional view of a deflector used with the prior art charged particle scanning apparatus.
Figure 5:
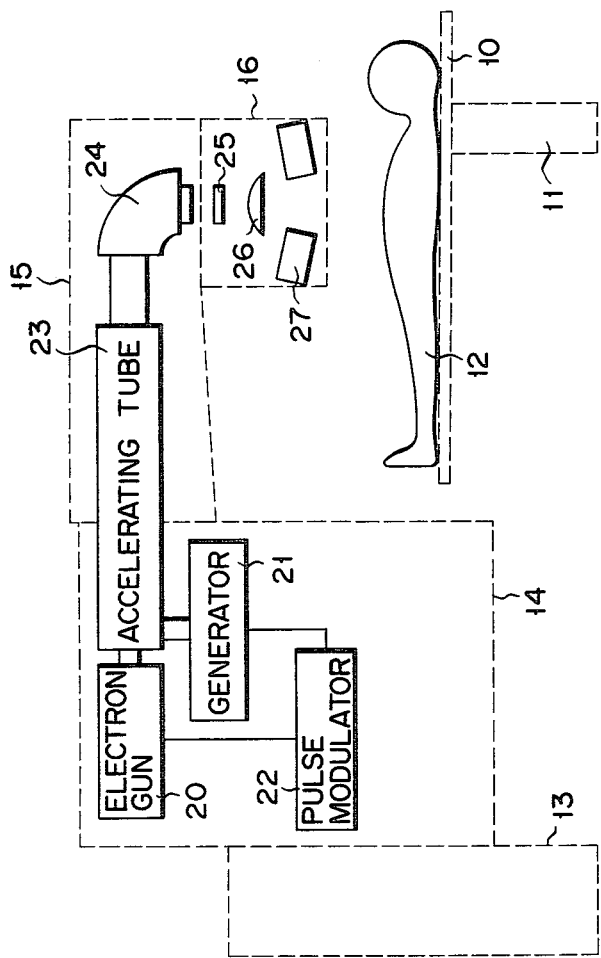
Figure 3:
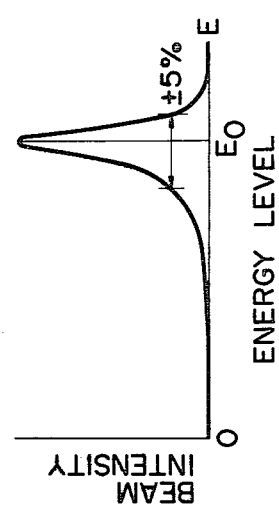
Figure 4:
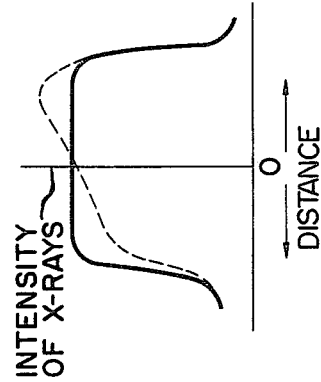
Figure 7:
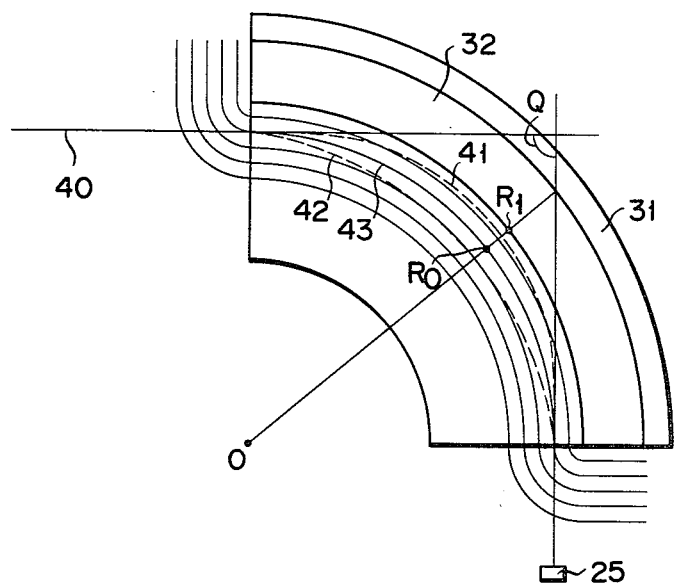
Figure 8:
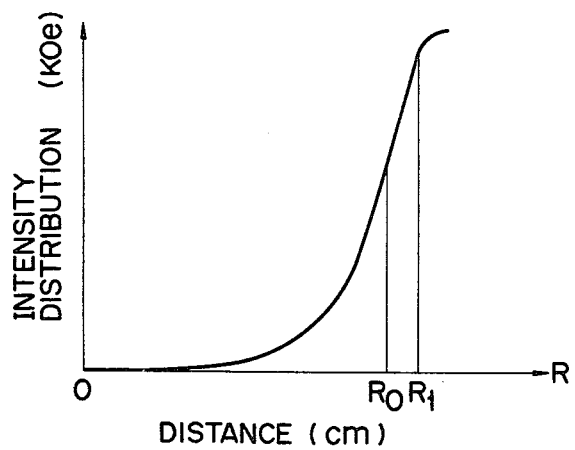
Figure 9:
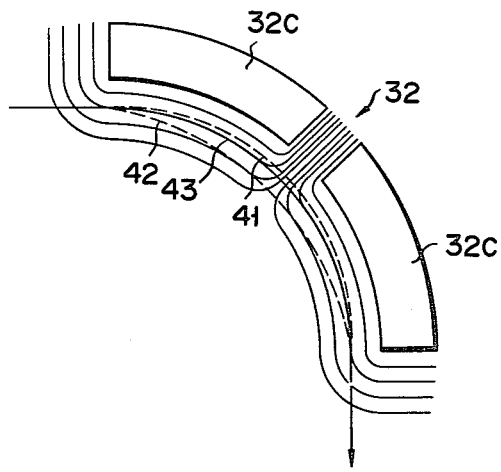
Figure 10:
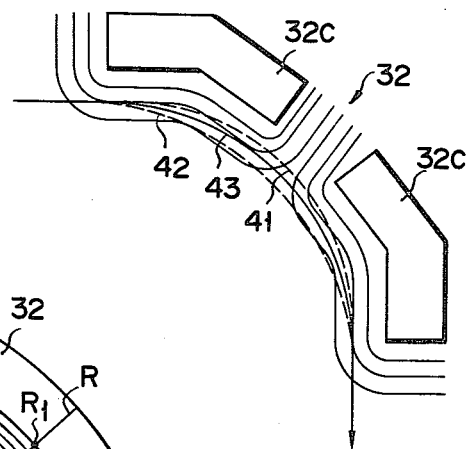
Figure 11:
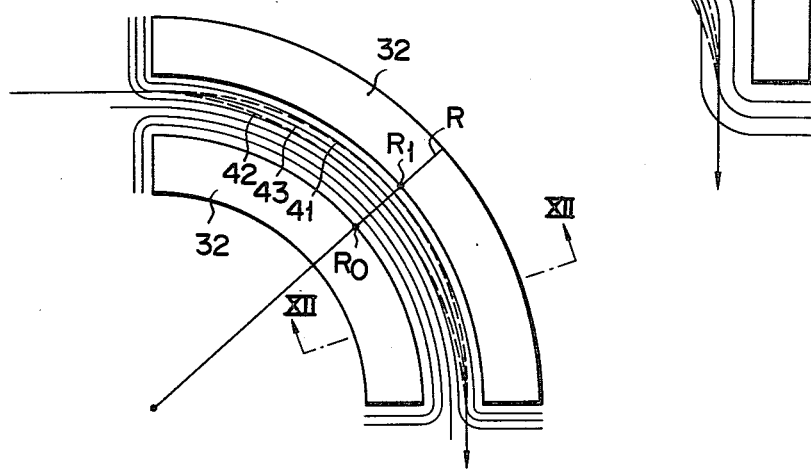
Figure 13:
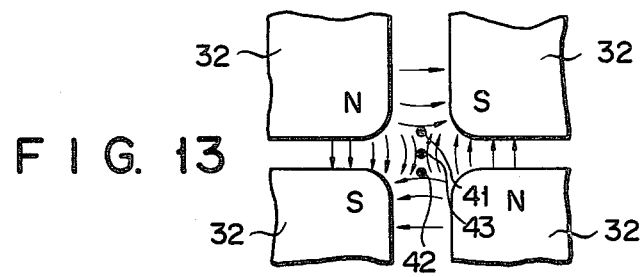
Figure 14:
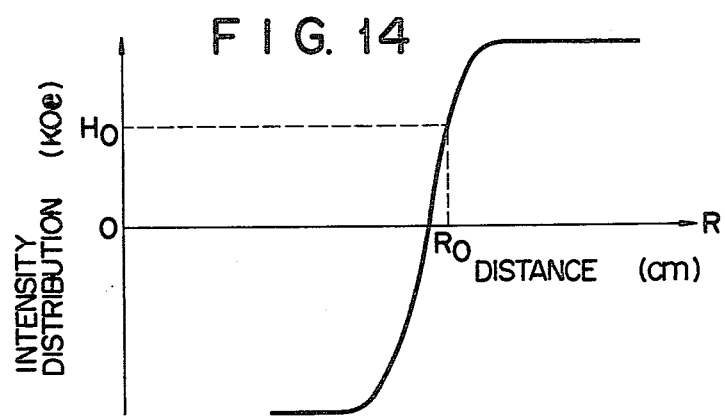
Figure 15:
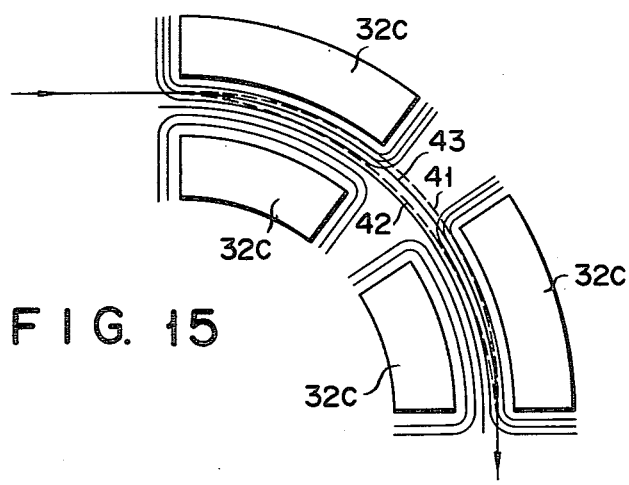

FIG. 3 graphically presents the distribution of the energies of electron beams deflected by the deflector of FIG. 1;

FIG. 4 graphically indicates the distribution in a foreground subject of the energies of X-rays obtained by impinging an electron beam deflected by the deflector of FIG. 1 on an X-ray target;

FIG. 5 schematically illustrates an X-ray irradiating apparatus using an electron beam scanning device according to one embodiment of this invention;

FIG. 6 is a schematical cross sectional view of a deflector used with the X-ray irradiating apparatus of FIG. 5;

FIG. 7 is a schematic side view of the deflector of FIG. 5 illustrating its operation;

FIG. 8 is a curve diagram showing the distribution of the intensity of a magnetic field generated in the deflector of the invention;

FIGS. 9 and 10 show the beams of charged particles corresponding to modifications of the magnetic pole arrangement applied in the deflector of the first embodiment;

FIGS. 11 to 14 are related to the other embodiment, wherein FIG. 11 is a graph showing an intensity distribution of a magnetic field, FIG. 12 is a schematical cross sectional view along lines XII—XII, FIG. 13 is a view showing a magnetic field generated between the magnetic poles and FIG. 14 is a graph showing a distribution of a magnetic field intensity; and FIG. 15 shows a magnetic pole arrangement modified from that which is used with the magnetic field generator of FIG. 11.

There will now be described a charged particle scanning apparatus according to one embodiment of this invention which is applied to a rotary X-ray irradiating apparatus for medical treatment.

Referring to FIG. 5, referential numeral 10 denotes a treatment couch rotatably supported by a support 11. A foreground examinee 12 is placed on said couch 10. A fixed gantry 13 is set behind the couch 10. Provided ahead of this fixed gantry 13 is a rotatable gantry 14 turned about a horizontal axis. A supporting arm 15 projects from the rotatable gantry 14 to extend above the foreground examinee 12. A treating head 16 is fitted to the extension end of said supporting arm 15 so as to face the examinee 12. The treating head 16 is rotated about the examinee 12 by the rotatable gantry 14. The support means, rotating mechanism and drive source of said rotation all for the rotatable gantry 14 may be formed of the known type, description thereof being omitted.

The rotatable gantry 14 receives an electron gun 20, a large power microwave generator 21 for acceleration and a pulse generator 22 for the electron gun 20 and microwave generator 21. An accelerating tube 23 is extended to the supporting arm 15 from the rotatable gantry 14. The above-mentioned acceleration device is of the ordinary type in which electron beams emitted from the electron gun 20 are accelerated into high energy in the accelerating tube 23 by large power microwaves issued from the microwave generator 21.

The later described deflector 24 is disposed ahead of the accelerating tube 23. This deflector 24 deflects an electron beam sent forth from the accelerating tube 23 at an angle of substantially 90° toward an X-ray target 25. The treatment head 16 contains said target 25, an X-ray flattening filter 26 and collimator 27 both positioned in front of the deflector 24. Thus, X-rays emitted from the target 25 by impingement of electron beams are directed to the examinee 12 through the filter 26 and collimator 27.

The deflector 24 comprises a deflection pipe 31 made of, for example, stainless steel and having a rectangular cross section as shown in FIG. 6, and downward deflects an electron beam passing through said deflection pipe 31 toward the surface of the drawing at an angle of substantially 90° around a reference axis. To effect this deflection, a magnetic field generator is so disposed as to bridge the deflection pipe 31. This generator comprises a yoke 33 provided with a pair of magnetic poles 32 mutually facing across said deflection pipe 31 and a pair of electromagnetic coils 34 wound about the yoke 33. Each magnetic pole 32 comprises a vertical end face 32a parallel with the outer wall of the deflection pipe 31 and an inclined plane 32b which lies below said vertical end face 32a and is inclined progressively downward toward the magnetic coil 34. As the result, the prescribed shortest space is allowed between the paired mutually facing vertical end faces 32a and a progressively downward broadening space is provided between the paired inclined planes 32b. A magnetic field created by the magnetic field generator constructed as described above arises, as shown in FIG. 7, along the paired magnetic poles 32, that is, along the outer walls of the deflection pipe 31. That portion of the magnetic field which lies between the mutually facing vertical end faces 32a has the highest intensity, and those portions of said magnetic field which occupy the lower space have a lower intensity as shown in FIG. 8.

As apparent from FIG. 7, the deflection pipe 31 and magnetic pole 32 are curved throughout the length at an angle of substantially 90° around a reference axis. The accelerating tube 23 is positioned on that side of the deflection pipe 31 at which an electron beam is introduced. The X-ray target 25 is disposed on that side of the deflection pipe 31 from which an electron beam is given off.

With the deflector 24 constructed as described above, an incoming beam 40 is deflected in the deflection pipe 31 such that, initially as in the prior art scanning device, a beam 41 having a higher energy $E_1$ occupies the outermost position; another beam 42 having a lower energy $E_2$ takes the innermost position; and still another beam 43 having the most probable energy $E_0$ passes along a route lying substantially between said outer and inner beams 41, 42. However, with the deflector of this invention, while the respective electron beams run through the deflection pipe 31, the higher energy beam 41 is strongly bent by the outer stronger portion of the magnetic field, and conversely the lower energy beam 42 is gently bent by the inner weaker portion of the magnetic field. In other words, deflector 24 causes an orbit of incoming beam 40 with a magnetic field whose intensity distributes along the orbit and is higher on the outer side of the orbit around the reference axis than that on the inner side. Eventually, therefore, when brought to the outlet of the deflection pipe 31, the introduced electron beam have been focussed rather than that entering the deflection pipe 31. Since the X-ray target 25 is irradiated by electron beams lying under such condition, X-rays emitted from the target 25 indicate a substantially uniform distribution of intensity.

There will now be detailed by reference to FIG. 8 the advantageous effect of this invention. FIG. 8 graphically shows the distribution H(R) of the intensity of a magnetic field acting in the direction of the curvature radius R of the curved magnetic pole 32. Referential numeral $R_1$ denotes the radius of the surface 32a of the curved magnetic pole 32; and $R_0$ is the radius of an orbit along which a beam formed of the largest number of electrons and having most probable energy $E_0$ is deflected. The center of the deflection orbit substantially coincides with the center of the curvature of the curved magnetic pole 32. Referring to FIG. 8, distances covered by the radii $R_0$, $R_1$ are plotted on the abscissa, and the distribution of the intensity of an electron beam is shown on the ordinate.

Now H and $R_0$ are so determined that the energy $E_0$ (MeV) of an accelerated electron beam and the intensity $H(R_0)$ (KOe) of a fringing field at the end of the radius $R_0$ (cm) of the deflection orbit have a relationship expressed by the following formula:

$$H(R_0) \cdot R_0 = 10/3\sqrt{E_0^2 + 1.025 E_0} \quad (1)$$

Where, in this case, an accelerated electron having an energy $E_0$ is introduced into the deflection pipe 31 in the direction of a tangent of a circle having the same radius as the curvature radius $R_0$ of the deflection orbit, then said beam runs along said deflection orbit. Where, in this case, the energy of the beam of accelerated charged particles increases to the level of $E_1$, then the right side term of the above-mentioned formula (1) has a larger value than the left side term. Accordingly, the accelerated electron beam passes along the outside of the above-mentioned deflection orbit, and consequently is deflected inward under a strong magnetic force. Conversely where an accelerated electron beam has a lower energy than the most probable energy $E_0$ of a beam formed of the largest number of electrons, then the beam of accelerated charged particles passes along the inside of the deflection orbit and consequently is less deflected under a weak magnetic force. When, therefore, the distribution H(R) of the intensity of a magnetic field is properly chosen in consideration of the deflection orbit radius $R_0$ of a beam formed of the largest number of electrons, the most probable energy $E_0$ of the accelerated electron beam and the deflection angle $\theta$ (FIG. 7), then it is possible always to cause an electron beam to be deflected to the prescribed position at the specified angle θ, regardless of changes in the energy of said beam.

Now assuming H(R)=6.03R−33.81[KOe]; and $R_0=6.5$ (cm) and $E_0=10$(MeV) in case R approximates $R_0$, then it is possible to limit changes in the position of a beam of charged particles just in front of an X-ray target within the range of ±0.5 (mm) and restrict changes in the deflection angle θ of said beam within the range of ±0.5 degrees even when energy of the beam changed by ±20 percent. Even where, therefore, changes arise in the energy of an electron beam due to minute fluctuations in the operation conditions such as the frequency and output of microwaves and the intensity of an electron beam corresponding to the frequency spectrum of said microwaves, little variation takes place in the distribution of the intensity of a deflected beam. Therefore, it has become possible to irradiate a uniform beam of charged particles exactly on the desired spot of a foreground subject and reduce the entire size of a scanning apparatus. It will be noted that even when curved, the inclined plane 32b (FIG. 6) of a magnetic pole 32, can attain substantially the same effect as described above.

The magnetic pole assembly 32 of the charged particle scanning apparatus of this invention may be formed, as shown in FIG. 9, of a plurality of (two in this embodiment) magnetic pole units 32c arranged lengthwise of a curved deflection pipe. Or it is possible, as seen from FIG. 10, to bend the inner plane of each magnetic pole unit 32c straight forward several times, instead of rounding it, thereby causing the magnetic pole assembly 32 as a whole to generate a magnetic field whose distribution presents an angular pattern.

According to the embodiments of FIGS. 9 and 10, a pair of magnetic pole units 32c are arranged in consideration of the shape of the entire magnetic pole assembly 32 and the positions of said magnetic pole units 32c relative to the deflection pipe 31 in order to cause a magnetic field produced to get weaker toward the inner side. However, any other type of a magnetic field generator may be adapted, provided it is possible to create a magnetic field achieving the same effect as the abovementioned form of magnetic field.

There will now be described the latter case by reference to FIGS. 11 and 12. Two curved cores 33 set one atop another are provided on each side of the curved deflection pipe 31. Each group of the cores 33 comprises a pair of magnetic poles 32 disposed on each side of the deflection pipe 31 to face each other at the prescribed space. The respective groups of the paired magnetic poles 32 as counted in the horizontal direction face each other across the deflection pipe 31. The four magnetic poles 32 are divided into a first group disposed in the upper or outer position and a second group arranged in the lower or inner position. Each core 33 is wound with an electromagnetic coil 34 to produce a magnetic field. The first group of the paired magnetic poles 32 cooperate to deflect that portion of an electron beam passing through the deflection pipe 31 which tends to be widely swerved toward the center of said beam. The second group of the paired magnetic poles 32 cooperate to deflect that portion of an electron beam running through the deflection pipe 31 also toward the center of said beam. With the embodiment of FIG. 12, the left side one of the first group of the paired magnetic poles 32 denotes the south pole, and the right side one the north pole. Conversely, the left side one of the second group of the paired magnetic poles 32 represents the north pole, and the right side one the south pole. A magnetic field produced among the four magnetic poles 32 thus arranged has such a distribution as illustrated in FIG. 13. The intensity of a deflected magnetic field has such a distribution as indicated in FIG. 14. In this drawing, the curvature radius of the curved magnetic pole 32 is plotted on the abscissa, and the distribution of the intensity of a magnetic field on the ordinate as in FIG. 8. As seen from FIGS. 13 and 14, a magnetic field acting in the direction of the radius of the central deflection orbit sharply changes according to the curvature radius R of the curved magnetic pole 32, thereby causing an electron beam to be deflected toward the central deflection orbit. Where, in this case, too, the intensity of a magnetic field is chosen to have a proper distribution H(R), then it is possible to cause an electron to be deflected to the prescribed position at the specified deflection angle θ, regardless of changes in the energy of said beam. In the embodiment of FIGS. 11 to 14, each magnetic pole assembly may be formed of a plurality of magnetic pole units 32c as shown in FIG. 15.

All the foregoing embodiments refer to the case where the charged particle scanning apparatus of this invention is applied to a medical treatment device which is designed to emit X-rays by impingement of accelerated charged particles on an X-ray target and irradiate X-rays on a foreground subject. However, the charged particle scanning apparatus of the invention may also be used with a device designed to irradiate an electron beam directly on a foreground subject. The charged particle scanning apparatus of the invention has to be provided with a microwave linear accelerator which is compact and yet can accelerate electrons into high energy.

What is claimed is:

1. A charged particle beam scanning apparatus comprising a charged particle source for emitting a beam of charged particles; a linear accelerator for accelerating a beam of charged particles issued from said charged particle source; and a deflection device for directly receiving a beam of accelerated charged particles from said accelerator and deflecting it, at an angle of less than 180° around a reference axis, said deflection device including a magnetic field generator to cause an orbit of said beam of charged particles with a magnetic field whose intensity distributes along said orbit and is higher on the other side of said orbit around said reference axis than that on the inner side thereby to prevent said beam of charged particles from diverging to different energy levels of the charged particles.

2. The charged particle scanning apparatus according to claim 1, wherein the deflection device comprises a deflection pipe through which a beam of charged particles passes; and the magnetic field generator comprises cores disposed on both sides of the deflection pipe, a pair of magnetic poles facing each other across the deflection pipe, and an electromagnetic coil wound about the cores to generate a magnetic field between the magnetic poles.

3. The charged particle scanning apparatus according to claim 2, wherein each of the paired magnetic poles has an inclined plane which is more widely spaced from that of the other magnetic pole in the direction in which a beam of charged particles is deflected.

4. The charged particle scanning apparatus according to claim 2, wherein each magnetic pole has an end face extending in the direction in which the beam of charged particles is deflected.

5. The charged particle scanning apparatus according to claim 4, wherein the end face of each of the paired magnetic poles is provided with a curved plane having the prescribed curvature radius.

6. The charged particle scanning apparatus according to claim 4, wherein the end face of each of the paired magnetic poles is provided with a plane bent straight forward several times.

7. The charged particle scanning apparatus according to claim 4, wherein the magnetic pole assembly has a plurality of magnetic pole units arranged in the direction in which the beam of charged particles is deflected.

8. The charged particle scanning apparatus according to claim 1, wherein the deflection device comprises an auxiliary magnetic field generator designed to produce in the direction in which the beam of charged particles is deflected a strong magnetic field acting in a direction opposite to that in which a magnetic field created by the major magnetic field generator is operated.

9. The charged particle scanning apparatus according to claim 1, which further comprises an X-ray target for emitting X-rays by impingement of a beam of charged particles deflected by the deflection device.

10. The charged particle scanning apparatus according to claim 9, which further comprises a couch on which a foreground subject being examined by X-rays is to be seated; and a device for revolving the X-ray target and deflection device about said couch.

* * * * *